(12) United States Patent
Liu et al.

(10) Patent No.: US 8,372,830 B2
(45) Date of Patent: Feb. 12, 2013

(54) METHODS FOR USING VASOPRESSIN ANTAGONISTS WITH ANTHRACYCLINE CHEMOTHERAPY AGENTS TO REDUCE CARDIOTOXICITY AND/OR IMPROVE SURVIVAL

(75) Inventors: Yongge Liu, Rockville, MD (US); Junichi Kambayashi, Rockville, MD (US)

(73) Assignee: Otsuka Pharmaceutical Co., Ltd., Osaka (JP)

( * ) Notice: Subject to any disclaimer, the term of this patent is extended or adjusted under 35 U.S.C. 154(b) by 353 days.

(21) Appl. No.: 12/600,145

(22) PCT Filed: May 12, 2008

(86) PCT No.: PCT/US2008/063374
§ 371 (c)(1),
(2), (4) Date: Nov. 13, 2009

(87) PCT Pub. No.: WO2008/144269
PCT Pub. Date: Nov. 27, 2008

(65) Prior Publication Data
US 2010/0249104 A1    Sep. 30, 2010

Related U.S. Application Data

(60) Provisional application No. 60/938,089, filed on May 15, 2007.

(51) Int. Cl.
*A61K 31/55* (2006.01)
*A61K 31/13* (2006.01)

(52) U.S. Cl. .............. 514/212.01; 514/214.01; 514/579; 514/645

(58) Field of Classification Search ............. 514/212.01, 514/214.01, 579, 645
See application file for complete search history.

(56) References Cited

U.S. PATENT DOCUMENTS

| | | | |
|---|---|---|---|
| 5,744,455 | A | 4/1998 | Speyer et al. |
| 2005/0187210 | A1 | 8/2005 | Ozaki et al. |

OTHER PUBLICATIONS

Orlandi et al. "Tolvaptan for the treatment of hyponatremia and congestive heart failure". Future Cardiol. (2006) 2(6), 627-634.*
Brenner B. et al., "The Cell Biology of Vasopressin Action", The Kidney. vol. 1, 7th ed. Chapter 13, p. 573-597, Philadelphia, PA, Saunders; 2004.
Talmi YP et al., "Syndrome of Inappropriate Secretion of Arginine Vasopressin in Patients With Cancer of the Head and Neck", Ann Otol Rhinol Laryngol Nov. 1992; 101 (11): 946-949.
Lemmens-Gruber R., et al., "Vasopressin Antagonists" CMLS Cellular and Molecular Life Sciences, vol. 63, No. 15, 2006, p. 1766-1779.

European Search Report dated Jul. 22, 2010 issued in corresponding Application No. 08755284.0-2123.
Christiansen, S. et al., Doxorubicin in experimental and clinical heart failure, European Journal of Cardiothoracic Surgery, 30 (Aug. 2006)611-616.
Swain, S. et al., Congestive Heart Failure in Patients Treated with Doxorubicin: a retrospective analysis of three trials, Cancer, Jun. 1, 2003; 97(11), pp. 2869-2879.
Singal, P. et al., Doxorubicin-Induced Cardiomyopathy, The New England Journal of Medicine, Sep. 24, 1998,339(13), pp. 900-905.
Krischer, J.P. et al., Clinical Cardiotoxicity Following Anthracycline Treatment for Childhood Cancer: The Pediatric Oncology Group Experience, Journal of Clinical Oncology, vol. 15, No. 4, Apr. 1997, pp. 1544-1552.
Lipshultz, S. E et al., The Effect of Dexrazoxane on Myocardial Injury in Doxorubicin-Treated Children with Acute Lymphoblastic Leukemia, The New England Journal of Medicine, Jul. 8, 2004, 351(2), pp. 145-153.
Cvethovic, R. et al., Dexrazoxane: A Review of its Use for Cardioprotection During Anthracycline Chemotherapy, Drugs, 2005, vol. 65, Issue 7, pp. 1005-1024.
Swain, S. M. et al., Cardioprotection With Dexrazoxane for Doxorubicin-Containing Therapy in Advanced Breast Cancer, Journal of Clinical Oncology, vol. 15, No. 4, Apr. 1997: pp. 1318-1332.
Tang, W. H. et al., Vasopressin receptor antagonists in the management of acute heart failure, Expert Opinion Investig. Drugs (2005) 14(5): pp. 593-600.
Campling, B. G. et al., Secretion of Atrial Natriuretic Peptide and Vasopressin by Small Cell Lung Cancer, Cancer, vol. 75, May 15, 1995, pp. 2442-2451.
Mizobuchi, M. et al., Syndrome of Inappropriate Secretion of ADH (SIADH) due to Small Cell Lung Cancer with Extremely High Plasma Vasopressin Level, Internal Medicine, vol. 33, No. 8, Aug. 1994, pp. 501-504.
North, W. G., Gene regulation of vasopressin and vasopressin receptors in cancer, Experimental Physiology, Mar. 2000, 85S, pp. 27S-40S.
North, W. G. et al., Vasopressin gene related products are markers of human breast cancer; Breast Cancer Research and Treatment, Jun. 1995,(34)3, pp. 229-235.
Umemura, S. et al., Serum level of arginine-vasopressin influences the prognosis of extensive-disease small-cell lung cancer, Journal of Cancer Research Clinical Oncology, Aug. 2007, 133(8), pp. 519-524.
Fan, M. J. et al., Messenger RNA expressions of vasopressin system and aquaporin-2 in adriamycin-induced nephrotic rats and effects of astragalus membranaceus, Chinese Medical Journal, Dec. 1999, 112(12), pp. 1068-1072.
Johnston, C. I. et al., Role of Vasopressin in Experimental Congestive Cardiac Failure, Journal of Cardiovascular Pharmacology, 1986, 8 Suppl (7), pp. S96-100.
Price, J. F. et al., Arginine Vasopressin Levels Are Elevated and Correlate With Functional Status in Infants and Children With Congestive Heart Failure, Circulation, May 17, 2004, pp. 2550-2553.

(Continued)

*Primary Examiner* — Renee Claytor
(74) *Attorney, Agent, or Firm* — Sughrue Mion, PLLC

(57) ABSTRACT

The present invention relates to methods of reducing cardiotoxicity and/or improving survival from treatment with anthracycline agents comprising administering a therapeutically effective amount of a composition comprising a vasopressin antagonist compound or a pharmaceutically acceptable salt thereof as an active ingredient, administered simultaneously or prior to the anthracycline administration.

16 Claims, 14 Drawing Sheets

OTHER PUBLICATIONS

Burrell, L. M. et al., Long-term effects of nonpeptide vasopressin $V_2$ antagonist OPC-31260 in heart failure in the rat, American Journal of Physiological Society, Jul. 1998, 275(1 Pt. 2):H176-H182.

Francis, G. S. et al., Vasopressin Receptor Antagonists, vol. 291, No. 16, JAMA, Apr. 28, 2004, pp. 2017-2018.

Xu, D. L. et al., Upregulation of Aquaporin-2 Water, Channel Expression in Chronic Heart Failure Rat, Journal of Clinical Investigation, vol. 99 No. 7, Apr. 1997, pp. 1500-1505.

Burrell L. M. et al., Vasopressin receptor antagonism—a therapeutic option in heart failure and hypertension, Experimental Physiology, 2000, 85S, 259S-265S.

Gheorghiade, M. et al., Vasopressin $V_2$-Receptor Blockade With Tolvaptan in Patients With Chronic Heart Failure: Results From a Double-Blind, Randomized Trail, Circulation, Jun. 3, 2003, 107, 2690-2696.

Takeuchi, M. et al., Effects of long-term oral treatment with selective vasopressin V2 receptor antagonist (OPC-31260) on adriamycin-induced heart failure in rats, International Journal of Cardiology 108(2), Jul. 6, 2005, pp. 231-236.

Iarussi, D. et al., Anthracycline-induced cardiotoxicity in children with cancer: strategies for prevention and management. *Pediatric Drugs* 2005;7(2):67-76.

* cited by examiner

Dox: doxorubicin. Tol: tolvaptan. Veh: vehicle.

Kaplan-Meier Survival Analysis of tolvaptan-treated rats.

Dox: doxorubicin. Tol: tolvaptan. Veh: vehicle.

Protocol for the DDAVP study

Dox: doxorubicin.

Dox: doxorubicin.

Kaplan-Meier survival analysis of doxorubicin treated rats.

Blood sampling protocol

- Dox: doxorubicin 2.5 mg/kg intraperitoneal injection 20 min prior to Veh or Tol
- Tol: tolvaptan 10 mg/kg. Veh: vehicle 1 % hydroxypropylmethylcellulose
- Heparinized Blood samples withdrawn 20 min after Tol or Veh on day 1 or day 13.

Veh: vehicle, Tol: tolvaptan

Tox: tolvaptan. Dox: doxorubicin. Veh: vehicle.

Dox: doxorubicin. Veh: vehicle.

Ejection Fraction of the Left Ventricle

Tox: tolvaptan. Dox: doxorubicin. Veh: vehicle.

Left ventricle end-diastolic volume/weight adjusted.

Tol: tolvaptan. Dox: doxorubicin. Veh: vehicle.

Left ventricle end-diastolic diameter/weight adjusted.

Tol: tolvaptan. Dox: doxorubicin. Veh: vehicle.

Improvement of Contractility Index

Tol: tolvaptan. Dox: doxorubicin. p<0.02 when the survival rates were compared using the Log-Rank test.

Kaplan Meier Survival Analysis.

METHODS FOR USING VASOPRESSIN ANTAGONISTS WITH ANTHRACYCLINE CHEMOTHERAPY AGENTS TO REDUCE CARDIOTOXICITY AND/OR IMPROVE SURVIVAL

This application claims priority to U.S. Provisional App. Ser. No. 60/938,089 filed May 15, 2007, which is incorporated herein by reference.

TECHNICAL FIELD

The present invention relates to a method of using vasopressin antagonists to reduce cardiac toxicity and/or improve survival in patients treated with anthracycline chemotherapy agents, such as doxorubicin (Adriamycin®), comprising administering to a patient a therapeutically effective amount of a composition comprising as an active ingredient a vasopressin antagonist compound, simultaneously or prior to the anthracycline administration, and to compositions useful therefor.

BACKGROUND OF THE INVENTION

Anthracycline agents are antineoplastic and used in chemotherapy for the treatment of a broad spectrum of hematogenous and solid human malignancies, including breast cancer and leukemia. However, the utility of anthracyclines such as doxorubicin (Adriamycin®) is limited by cumulative and dose-related myocardial damage that may lead to congestive heart failure (CHF).[1,2] It has been estimated that up to 20% of the patients treated with doxorubicin may develop CHF.[3]

In addition to cumulative dose, age, combination therapy, hypertension, liver disease, chest-wall radiation from previous cancer treatment and preexisting cardiac disease are added risk factors for doxorubicin-induced CHF.[4]

Despite its known cardiotoxicity, doxorubicin is one of the most widely used chemotherapy agents due to its effectiveness to prolong the life of cancer patients. It has been estimated that more than 50% of long-term survivors of childhood cancer were treated with doxorubicin or another anthracycline.[5] However, many of the survivors who were treated with doxorubicin have long-term problems, often manifested as cardiac diseases. They often present as EKG changes and arrhythmias, or as a cardiomyopathy leading to CHF, as well as an increased risk of sudden death and death from cardiac causes.[6]

Doxorubicin-induced cardiotoxicity is related to a patient's cumulative lifetime dose of doxorubicin. CHF is characterized by the reduced ability of the heart to pump blood, resulting in fluid retention and detrimental neuro-hormonal activation. Left untreated, CHF patients have a very high mortality rate. The underlying mechanism of this doxorubicin-induced cardiotoxicity is not clear. The only effective strategy of reducing the doxorubicin cardiotoxicity is to limit the exposure of doxorubicin. But this also limits the effectiveness of doxorubicin for treating the cancer.

Dexrazoxane (Zinecard®) is currently the only approved drug treatment for reducing anthracycline-induced cardiotoxicity with very limited benefits.[6-8] Thus, there is an urgent and unmet medical need to develop treatments that are able to reduce doxorubicin-induced cardiotoxicity. Reducing the toxicity will also allow higher doses of doxorubicin to be safely administered to cancer patients.

Vasopressin (also known as antidiuretic hormone (ADH)) is a small nine-amino-acid peptide synthesized in the hypothalamus supraoptic and paraventricular nuclei and stored in the posterior pituitary. Its release is regulated by plasma osmolarity and blood volume/pressure.[9] Vasopressin causes vasoconstriction via $V_1$ receptors in vascular smooth muscle cells and water retention via $V_2$ receptors in the kidney collecting ducts.[10]

Vasopressin levels are frequently elevated in cancer patients.[11-14] Hyponatremia, due to abnormally high levels of vasopressin, is also very common in patients with cancer.[12,15] Furthermore, high serum vasopressin levels have been shown to be correlated to the low survival rate of small-cell lung cancer patients,[16] indicating a detrimental role of vasopressin in cancer patients.

Studies have shown that doxorubicin may increase the level of vasopressin. In doxorubicin-treated rats, the expression of vasopressin and aquaporin-2 water channel, which transport water from a collecting duct in the kidney to the blood circulation, is elevated.[17] Furthermore, doxorubicin-treated rabbits have an increased sensitivity to vasopressin.[18]

Accumulating evidence suggests that vasopressin may play an important role in the development and progression of CHF: vasopressin and aquaporin-2 water channel levels are increased in CHF[19-22] and $V_2$ antagonists have shown benefits in lessening congestion and improving symptoms in subjects with CHF.[23,24] Water retention and systemic edema are the hallmarks of CHF.

Previously, a few studies investigated the potential of vasopressin antagonists to reduce doxorubicin-induced cardiac injury and to promote survival in experimental animals. It was found that vasopressin antagonists may alleviate the symptoms of CHF[18] caused by doxorubicin injection. However, in a previous study, OPC-31260, a vasopressin $V_2$ receptor antagonist, had a slight but not significant reduction of mortality rate in doxorubicin-treated rats.[25] Thus, although these studies demonstrated benefits of vasopressin antagonists in treating doxorubicin-induced toxicity, the effects were not remarkable. In these previous studies, vasopressin antagonists were given several weeks after the administration of doxorubicin. Thus, permanent myocardial injury may have already occurred before the initiation of vasopressin antagonist therapy. Importantly, models in these previous studies may not faithfully reproduce an elevated vasopressin environment as often found in cancer patients since only normal healthy rats were used. An experimental model with elevated vasopressin may be ideal for the evaluation of the therapeutic potential of $V_2$ antagonists.

SUMMARY OF THE INVENTION

The present inventors have found that vasopressin antagonist compounds are effective for reducing cardiotoxicity and/or improving survival in subjects treated with anthracyclines, such as doxorubicin, chemotherapy treatments, if the vasopressin antagonists are administered simultaneously with or prior to anthracycline administration.

Thus, the present invention relates to a method for reducing cardiotoxicity and/or improving survival comprising administering a vasopressin antagonist compound simultaneously with or prior to administration of an anthracycline agent, such as doxorubicin, to a patient in need thereof. The methods and compositions of the present invention can be used to reduce chemotherapy-related side effects, such as cardiac injury, especially heart failure. The methods and compositions of the present invention can also be used to improve survival with doxorubicin therapy.

The present inventors have also found that vasopressin further increases the mortality rate in subjects treated with anthracyclines, such as doxorubicin. Thus, vasopressin antagonist compounds may be especially useful and effective in doxorubicin-treated patients with elevated vasopressin.

Thus, the present invention includes the following various embodiments.

In a first embodiment, the present invention provides a method for reducing cardiotoxicity and/or improving survival after an anthracycline anti-cancer treatment comprising administering to a patient in need thereof a therapeutically effective amount of a composition comprising a vasopressin antagonist compound or a pharmaceutically acceptable salt thereof as the active ingredient simultaneously with or prior to administration of the anthracycline agent.

In a second embodiment, the present invention provides a method according to the first embodiment, for reducing cardiotoxicity.

In a third embodiment, the present invention provides a method according to the first embodiment for improving survival.

In a fourth embodiment, the present invention provides a method according to the first embodiment, wherein the vasopressin antagonist is a compound represented by formula (I) or a pharmaceutically acceptable salt thereof.

In a fifth embodiment, the present invention provides a method according to the first embodiment, wherein the vasopressin antagonist is selected from the group consisting of, but not limited to, tolvaptan, mozavaptan, conivaptan, lixivaptan, satavaptan, RWJ-351647, RWJ-339489, SSR-149415, YM-222546, YM-471, YM-35471, YM-218, FR-218944, JNJ-17079166, JNJ-17308616, VMAX-367, VMAX-382, VMAX-372, ORG-52186, SRX-251 and pharmaceutically acceptable salts thereof.

In a sixth embodiment, the present invention provides a method according to the first embodiment, wherein the vasopressin antagonist is a $V_2$ selective vasopressin antagonist or a $V_1/V_2$ vasopressin antagonist.

In a seventh embodiment, the present invention provides a method according to the first embodiment, wherein an anthracycline consisting of daunorubicin, doxorubicin, epirubicin, and idarubicin simultaneously.

In an eighth embodiment, the present invention provides a method according to the first embodiment, wherein the vasopressin antagonist is tolvaptan.

In a ninth embodiment, the present invention provides a method according to the first embodiment, wherein the vasopressin antagonist is mozavaptan hydrochloride.

In a tenth embodiment, the present invention provides a method according to the first embodiment, wherein the vasopressin antagonist is conivaptan hydrochloride.

In an eleventh embodiment, the present invention provides a method according to the first embodiment, wherein the vasopressin antagonist is lixivaptan.

In a twelfth embodiment, the present invention provides a method according to the first embodiment, wherein the vasopressin antagonist is satavaptan.

In a thirteenth embodiment, the present invention provides a method according to the first embodiment, wherein the vasopressin antagonist is tolvaptan and the anthracycline is doxorubicin.

In a fourteenth embodiment, the present invention provides a method according to the first embodiment, wherein the vasopressin antagonist is tolvaptan and the anthracycline is daunorubicin.

In a fifteenth embodiment, the present invention provides a method according to the first embodiment, wherein the vasopressin antagonist is tolvaptan and the anthracycline is epirubicin.

In a sixteenth embodiment, the present invention provides a method according to the first embodiment, wherein the vasopressin antagonist is tolvaptan and the anthracycline is idarubicin.

In a seventeenth embodiment, the present invention provides a pharmaceutical composition comprising a vasopressin antagonist compound or a pharmaceutically acceptable salt thereof for reducing cardiotoxicity and/or improving survival from anthracycline chemotherapy for administering simultaneously or prior to anthracycline administration.

In an eighteenth embodiment, the present invention provides a pharmaceutical composition comprising a therapeutically effective amount of a vasopressin antagonist compound or a pharmaceutically acceptable salt thereof and a therapeutically effective amount of an anthracycline.

In a nineteenth embodiment, the present invention provides a use of a vasopressin antagonist compound or a pharmaceutically acceptable salt thereof for preparing a medicament for reducing cardiotoxicity and/or improving survival from anthracycline chemotherapy for administering simultaneously or prior to the anthracycline administration.

DETAILED DESCRIPTION OF THE INVENTION

Figure 1:
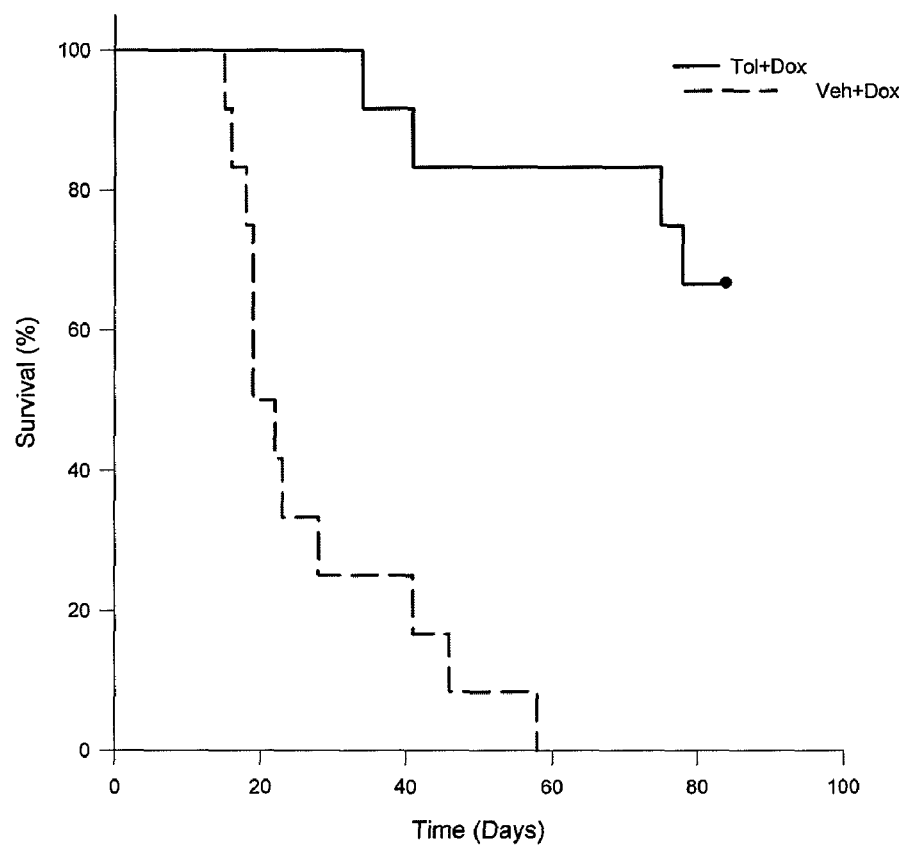
FIG. 1 shows a Kaplan-Meier Survival Analysis with the Log-Rank test of tolvaptan-treated rats.

Anthracycline agents are antineoplastic agents used in chemotherapy for the treatment of a broad spectrum of hematogenous and solid human malignancies, including breast cancer and leukemia. However, the utility of anthracyclines, such as doxorubicin (Adriamycin®), is limited by cumulative and dose-related myocardial damage.[2] Doxorubicin related toxicity often presents as EKG changes and arrhythmias, or as a cardiomyopathy leading to CHF, as well as an increased risk of sudden death and death from cardiac causes.[6]

The methods of the present invention are suitable for treating an individual afflicted with any neoplasia/cancer. The neoplastic cells killed by methods of the present invention include cells of tumors, neoplasms, carcinoma, sarcomas, papillomas, leukemia, lymphomas, and the like. Solid tumors are of particular interest.

As used herein, the term "cancer" encompasses any cell or cells whose normal growth control mechanisms are disrupted, thereby providing the potential for uncontrolled cell proliferation. The term "cancer" includes both benign and malignant neoplastic cells/tumors in both the nervous system and the periphery, wherein periphery is intended to mean all other parts of the body outside of the brain or spinal cord.

A "patient" as described herein includes one who has cancer such as leukemia, lymphomas, breast cancer, uterine cancer, ovarian cancer or lung cancer, and who is treated with an anthracycline agent.

The present invention also provides a method for the prevention and/or treatment of mammalian cardiac tissue damage such as cardiotoxicty caused by anthracycline antineoplastics such as doxorubicin.

"Cardiotoxicity" as used herein encompasses clinical heart failure, clinical cardiotoxicity such as acute heart failure and congestive heart failure and/or cardiac arrythmias and subclinical cardiotoxicity such as that detected by pathologic changes in cardiac biopsy and/or blood chemistry or decrease in ventricular ejection fractions.

The methods of the present invention may also be used for the increase of survival of the subjects during and after an anti-cancer treatment.

In a first embodiment of the present invention, the active ingredient in the method for reducing anthracycline treatment related cardiotoxicity of the present invention is a vasopressin antagonist compound. Vasopressin antagonist compounds of the present invention include, but are not limited to tolvaptan, mozavaptan, conivaptan, lixivaptan, satavaptan, RWJ-351647, RWJ-339489, SSR-149415, YM-222546, YM-471, YM-35471, YM-218, FR-218944, JNJ-17079166, JNJ-17308616, VMAX-367, VMAX-382, VMAX-372, ORG-52186, SRX-251, or pharmaceutically acceptable salts thereof and a benzoazepine compound or its salt described in WO 2007/074915, etc.

Vasopressin antagonist compounds of the present invention also include benzazepine compounds having activity as a vasopressin antagonist. Such benzazepine compounds have activity at arginine vasopressin (AVP) type 1A ($V_{1A}$) and type 2 ($V_2$) receptors (i.e., $V_1/V_2$) or are selective for the $V_2$ receptor. Benzazepine compounds of the present invention include but are not limited to compounds represented by the following formula (I):

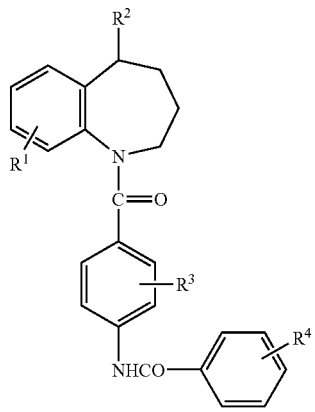

Formula (I)

wherein $R^1$ is a hydrogen atom or a halogen atom, $R^2$ is a hydroxy group, or a group of the formula: —$NR^5R^6$ wherein $R^5$ and $R^6$ are the same or different and are each a hydrogen atom or a lower alkyl group, $R^3$ is a hydrogen atom, a halogen atom, a lower alkyl group, or a lower alkoxy group, $R^4$ is a halogen atom, a lower alkyl group or a lower alkoxy group, or a pharmaceutically acceptable salt thereof.

In the description and claims, the groups in the above formula (I) denote the following groups.

The "halogen atom" denotes a fluorine atom, a chlorine atom, a bromine atom, or an iodine atom. The "lower alkyl group" denotes a straight chain or branched chain alkyl group having 1 to 6 carbon atoms, such as methyl, ethyl, propyl, isopropyl, butyl, tert-butyl, pentyl, or hexyl.

The "lower alkoxy group" denotes a straight chain or branched chain alkoxy group having 1 to 6 carbon atoms, such as methoxy, ethoxy, propoxy, isopropoxy, butoxy, tert-butoxy, pentyloxy, or hexyloxy.

The benzazepine compounds of the formula (I) and processes for preparing the same are disclosed in WO 91/05549, U.S. Pat. No. 5,258,510 and U.S. Pat. No. 5,753,677 as well as in the Japanese counterpart JP-A-6-80641, each of which are incorporated by reference in their entirety herein.

The benzazepine compounds of formula (I) of the present invention can readily form a pharmaceutically acceptable acid addition salt with a pharmaceutically acceptable acid. The pharmaceutically acceptable acids include inorganic acids, such as sulfuric acid, hydrochloric acid, phosphoric acid, hydrobromic acid, etc. and organic acids such as acetic acid, p-toluenesulfonic acid, methanesulfonic acid, oxalic acid, maleic acid, fumaric acid, malic acid, tartaric acid, citric acid, succinic acid, benzoic acid, etc.

Among the benzazepine compounds of the formula (I), the compounds having an acidic group can readily form a salt with a pharmaceutically acceptable basic compound. The basic compounds include metal hydroxides such as sodium hydroxide, potassium hydroxide, lithium hydroxide, calcium hydroxide, etc.; alkali metal carbonates or hydrogen carbonates, such as potassium carbonate, sodium carbonate, sodium hydrogen carbonate, potassium hydrogen carbonate, etc.; and alkali metal alcoholates such as sodium methylate, potassium methylate, etc.

The vasopressin antagonist compounds of formula (I) of the present invention are used in the form of a conventional pharmaceutical preparation. The preparation is prepared by using conventional diluents or carriers such as fillers, thickening agents, binders, wetting agents, disintegrators, surfactants, lubricants, and the like. The pharmaceutical preparations can be selected from various forms in accordance with the desired utilities, and the representative forms are tablets, pills, powders, solutions, suspensions, emulsions, granules, capsules, suppositories, injections (solutions, suspensions, etc.), and the like.

In order to form in tablets, there are used well known pharmaceutical carriers such as vehicles (e.g. lactose, white sugar, sodium chloride, glucose, urea, starch, xylitol, mannitol, erythritol, sorbitol, calcium carbonate, kaolin, crystalline cellulose, silicic acid, etc.), binders (e.g. water, ethanol, propanol, simple syrup, glucose solution, starch solution, gelatin solution, carboxylmethyl cellulose, shellac, methyl cellulose, potassium phosphate, polyvinylpyrrolidone, etc.), disintegrators (e.g. dry starch, sodium alginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium base, sodium laurylsulfate, etc.), wetting agents (e.g. glycerin, starches, etc.), adsorbents (e.g. starches, lactose, kaolin, bentonite, colloidal silicates, etc.), lubricants (e.g. purified talc, stearates, boric acid powder, polyethylene glycol, etc.), and the like. Moreover, the tablets may also be in the form of a conventional coated tablet, such as sugar-coated tablets, gelatin-coated tablets, enteric coated tablets, film coating tablets, or double or multiple layer tablets. In the preparation of pills, the conventional carriers can be used and include, for example, vehicles (e.g. glucose, lactose, starches, cacao butter, hydrogenated vegetable oils, kaolin, talc, etc.), binders (e.g. gum arabic powder, tragacanth powder, gelatin, ethanol, etc.), disintegrators (e.g. laminaran, agar, etc.) and the like. In the preparation of suppositories, the conventional carriers can be used and include, for example, polyethylene glycol, cacao butter, higher alcohol, higher alcohol esters, gelatin, semi-synthetic glycerides, and the like. Capsules can be prepared by charging a mixture of the compound of the present invention and the above carriers into hard gelatin capsules, soft capsules or hydroxypropylmethyl cellulose capsules (HPMC capsules) in usual manner. In the preparation of injections, the solutions, emulsions and suspensions are sterilized and are preferably made isotonic with the blood. In the preparation of these solutions, emulsions and suspensions, there are used conventional diluents such as water, ethyl alcohol, macrogol, propylene glycol, ethoxylated isostearyl alcohol, polyoxylated isostearyl alcohol, polyoxyethylene sorbitan fatty acid esters, and the like. In this case, the pharmaceutical preparations may also be incorporated with sodium chloride, glucose, or glycerin in an amount sufficient to make them isotonic, and may also be incorporated with conventional solubilizers, buffers, and anesthetizing agents. Moreover, the pharmaceutical preparations may optionally incorporate coloring agents, preservatives, perfumes, flavors, sweetening agents, and other medicaments, if required.

The amount of the vasopressin antagonist compounds of formula (I) to be incorporated into the pharmaceutical composition of the present invention may be selected from a broad range. Usually, the amount preferably in the range of 1 to 70% by weight, more preferably 5 to 50% by weight, based on the weight of the composition.

A suitable method for administration of the compositions of the present invention may be determined in accordance with various forms of preparations, ages, sexes and other conditions of the patients, the degree of severity of diseases, and the like. For example, tablets, pills, solutions, suspensions, emulsions, granules and capsules are administered orally. The injections are intravenously administered alone or together with a conventional auxiliary liquid (e.g. glucose, amino acid solutions), and further are optionally administered alone in intramuscular, intracutaneous, subcutaneous, or intraperitoneal route, if required. Suppositories are administered in intrarectal route.

The dosage of the vasopressin antagonist compounds of the present invention may be selected in accordance with the usage, ages, sexes and other conditions of the patients, the degree of severity of the diseases, and the like. A suitable dose is in the range of 0.1 mg to 1000 mg/body per day, preferably 0.5 mg to 500 mg/body per day, more preferably 1 mg to 100 mg/body per day.

Vasopressin antagonist compounds of the present invention include, but are not limited to tolvaptan, mozavaptan, conivaptan, lixivaptan and satavaptan, or a pharmaceutically acceptable salt thereof. Further, RWJ-351647 and 339489, SSR-149415, YM-222546, YM-471, YM-35471, YM-218, FR-218944, JNJ-17079166 and 17308616, VMAX-367, VMAX-382, VMAX-372, ORG-52186, SRX-251, etc., or pharmaceutically acceptable salts thereof may also be employed as a vasopressin antagonist in the present invention.

In another embodiment, the present invention provides a method for treating cancer comprising administering to a patient a therapeutically effective amount of a combination of a vasopressin antagonist compound and an anthracycline. The anthracyclines include, but are not limited to daunorubicin (Cerubidine®), doxorubicin (Adriamycin®, Rubex®), epirubicin (Ellence®, Pharmorubicin®), and idarubicin (Idamycin®). The combinations of the invention may include a pharmaceutically acceptable vehicle, carrier or diluent.

The selection of the dosage of the vasopressin antagonist compound and the anthracycline is that which can provide relief to the patient as measured by a reduction of cardiotoxicity from anthracycline treatment alone and/or improvement of the effectiveness of the cancer treatment. As is well known, the dosage of each component depends on several factors such as the potency of the selected specific compound, the mode of administration, the age and weight of the patient, the severity of the condition to be treated, and the like. This is considered to be within the skill of the artisan and one can review the existing literature regarding each component to determine optimal dosing.

The presently preferred vasopressin antagonist used according to the invention is tolvaptan. Tolvaptan, also called, 7-chloro-5-hydroxy-1-[2-methyl-4-(2-methylbenzoyl-amino)benzoyl]-2,3,4,5-tetrahydro-1H-benzazepine, is a selective vasopressin $V_2$ antagonist. Tolvaptan is represented by the following structure:

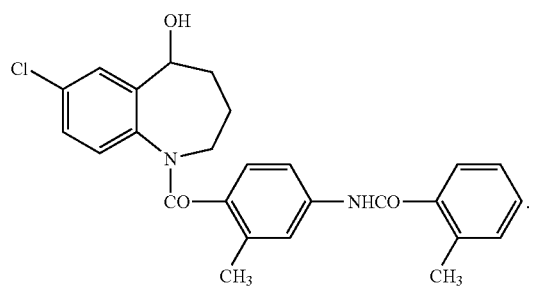

Tolvaptan generates increased, dose-dependent production of diluted urine without altering serum electrolyte balance, and without activation of renin-angiotensin system.

Other vasopressin antagonists which can be used include, but are not limited to: mozavaptan (described in U.S. Pat. No. 5,258,510, which is incorporated by reference herein in its entirety), conivaptan (described in U.S. Pat. No. 5,723,606, which is incorporated by reference herein in its entirety), lixivaptan (described in EP 636625 and U.S. Pat. No. 5,516,774, which are each incorporated by reference herein in their entirety) and satavaptan (described in WO971556, which is incorporated by reference herein in its entirety). Further, RWJ-351647 and 339489, SSR-149415, YM-222546, YM-471, YM-35471, YM-218, FR-218944, JNJ-17079166 and 17308616, VMAX-367, VMAX-382, VMAX-372, ORG-52186, SRX-251, and a benzoazepine compound or its salt described in WO2007/074915, etc., may also be employed as vasopressin antagonists in the present invention.

For use in medicine, pharmaceutically acceptable salts may be useful in the preparation of the vasopressin antagonist compounds according to the invention. The expression "pharmaceutically acceptable salts" includes both pharmaceutically acceptable acid addition salts and pharmaceutically acceptable cationic salts.

The term "therapeutically effective amount" as used herein refers to a sufficient amount of the compound to reduce infarction, such as for example, myocardial infarction, at a reasonable benefit/risk ratio applicable to any medical treatment.

The specific therapeutically effective dose level for any particular patient will depend upon a variety of factors including the severity of the condition; activity of the specific compound employed; the specific composition employed and the age of the subject. However, some variation in dosage will necessarily occur depending upon the condition of the subject being treated. The person responsible for administration will, in any event, determine the appropriate dose for the individual subject.

A combination of vasopressin antagonists and anthracyclines of the present invention can be administered in a standard manner such as orally, parenterally, transmucosally (e.g., sublingually or via buccal administration), topically, transdermally, rectally, via inhalation (e.g., nasal or deep lung inhalation). Parenteral administration includes, but is not limited to intravenous, intraarterial, intraperitoneal, subcutaneous, intramuscular, intrathecal, and intraarticular, or via a high pressure technique, like Powderject™.

For buccal administration, the composition can be in the form of tablets or lozenges formulated in conventional manner. For example, tablets and capsules for oral administration can contain conventional excipients such as binding agents (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate), or welting agents (for example, sodium lauryl sulfate). The tablets can be coated according to methods well known in the art.

Additionally, compositions of the present invention can be formulated for parenteral administration by injection or continuous infusion. Formulations for injection can be in the form of suspensions, solutions, or emulsions in oily or aqueous vehicles, and can contain formulation agents, such as suspending, stabilizing, and/or dispersing agents. Alternatively, the active ingredient can be in powder form for constitution with a suitable vehicle (e.g., sterile, pyrogen-free water) before use.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols.

Alternatively, the compounds of the present invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, such as suspending agents, such as sorbitol syrup, synthetic and natural gums such as tragacanth, acacia, alginate, dextran, sodium carboxymethylcellulose, methylcellulose, polyvinyl-pyrrolidone or gelatin, glucose/sugar syrup, gelatin, hydroxyethylcellulose, hydroxypropylmethylcellulose, aluminum stearate gel, emulsifying agents, such as lecithin, sorbitan monooleate, or acacia; nonaqueous vehicles (which can include edible oils), such as almond oil, fractionated coconut oil, oily esters, propylene glycol, and ethyl alcohol; and preservatives, such as methyl or propyl p-hydroxybenzoate and sorbic acid. The liquid forms in which the compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles.

When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

A combination of the vasopressin antagonists and anthracyclines of the present invention can also be administered in a controlled release formulation such as a slow release or a fast release formulation. Such controlled release formulations of the combinations of this invention may be prepared using methods well known to those skilled in the art. The method of administration will be determined by the attendant physician or other person skilled in the art after an evaluation of the patient's condition and requirements.

The pharmaceutical compositions of the present invention can consist of a combination of immediate release and controlled release characteristics. Such compositions can take the form of combinations of the active ingredients that range in size from nanoparticles to microparticles or in the form of a plurality of pellets with different release rates.

The combinations of this invention can also be administered in parenteral form. For parenteral administration, solutions in sesame or peanut oil or in aqueous propylene glycol can be employed, as well as sterile aqueous solutions of the corresponding water-soluble salts. Such aqueous solutions can be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

Methods of preparing various pharmaceutical compositions with a certain amount of active ingredient are known, or will be apparent in light of this disclosure, to those skilled in this art.

Pharmaceutical compositions according to the invention can contain 0.1%-95% of the therapeutic agents of this invention, preferably 1%-70%. In any event, the composition or formulation to be administered will contain a quantity of therapeutic agent(s) according to the invention in an amount effective to treat the condition or disease of the subject being treated.

The two different compounds of this invention, i.e., the vasopressin antagonist compound and the anthracycline, can be co-administered simultaneously or vasopressin first followed by an anthracycline.

The present invention is illustrated in more detail by the following Examples.

EXAMPLES

Example 1

Methods

Repeated injection of doxorubicin in animals is known to cause cardiac injury and to increase mortality. A study was designed to investigate the effect of tolvaptan on doxorubicin-induced cardiac toxicity and animal death. Four groups of rats were evaluated; all with 6 injections of doxorubicin (2.5 mg/kg each) during a two week period. To test the ability of tolvaptan to prevent toxicity, tolvaptan (10 mg/kg orally) daily was given to one group of rats (Tol+Dox). Another group of rats was given vehicle only (Veh+Dox). To test the ability of tolvaptan to reverse the toxicity, tolvaptan (10 mg/kg orally) daily was given to one group of rats, starting after the completion of doxorubicin administration (Dox+Tol). Another group of rats was given vehicle only (Dox+Veh). Table 1 summarizes the group designations:

TABLE 1

The treatment groups for the model of intraperitoneal injection of doxorubicin.

| Group Name | Drug Dose | Number of Rats |
|---|---|---|
| 1 Veh + Dox | Doxorubicin was injected 6 times (2.5 mg/kg each, intraperitoneally) during a 13 day period. Oral vehicle was given daily, starting with the first injection of doxorubicin. | 12 |
| 2 Tol + Dox | Doxorubicin was injected 6 times (2.5 mg/kg each, intraperitoneally) during a 13 day period. Oral tolvaptan (10 mg/kg) was given daily, starting with the first injection of doxorubicin. | 12 |
| 3 Dox + Veh | Doxorubicin was injected 6 times (2.5 mg/kg each, intraperitoneally) during a 13 day period. Oral vehicle was given daily, starting at the next day after the completion of 6 injections of doxorubicin. | 12 |

TABLE 1-continued

The treatment groups for the model of intraperitoneal injection of doxorubicin.

| Group Name | Drug Dose | Number of Rats |
|---|---|---|
| 4 Tol + Dox | Doxorubicin was injected 6 times (2.5 mg/kg each, intraperitoneally) during a 13 day period. Oral tolvaptan (10 mg/kg) was given daily, starting at the next day after the completion of 6 injections of doxorubicin. | 12 |

Dox: doxorubicin,
Tol: tolvaptan,
Veh: vehicle.

The rats were observed for 12 weeks. Survival was analyzed using Kaplan-Meier survival analysis with the Log-Rank test.

FIG. 1 shows that the mortality rate was significantly reduced by tolvaptan treatment ($p<0.001$).

Figure 2:
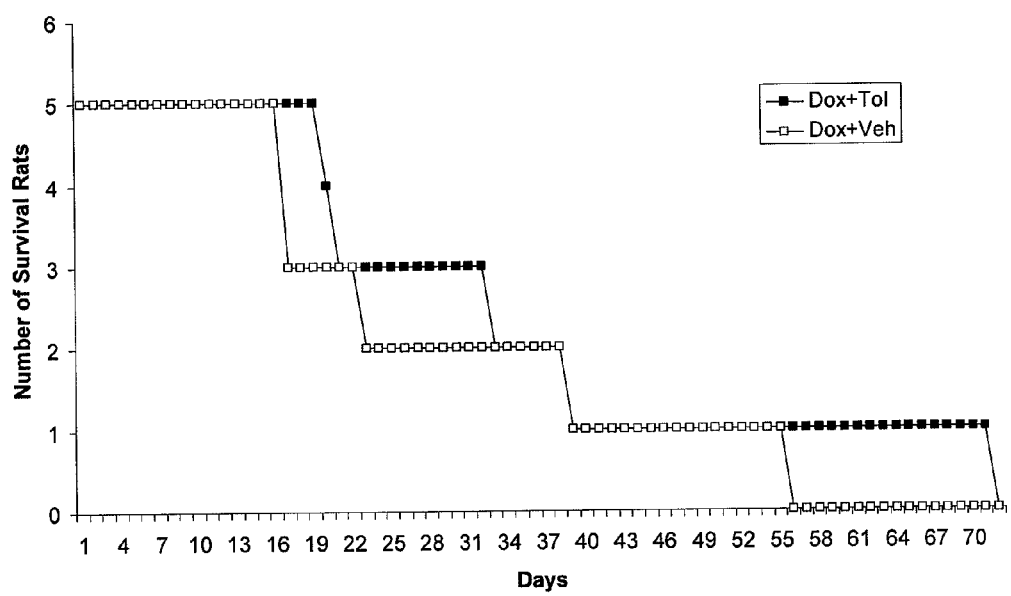
FIG. 2 is a graph showing the results of tolvaptan treatment starting after the completion of doxorubicin treatment.

When the treatment with tolvaptan was initiated after the completion of 6 injections of doxorubicin, the protective effect of tolvaptan was largely lost as can be seen in FIG. 2. There was only a small delay of rat death by tolvaptan. In the two groups of rats given doxorubicin and tolvaptan and the rats given doxorubicin and vehicle only, a total of 24 rats received doxorubicin injection. However, after the completion of doxorubicin administration, a significant number of the rats appeared very sick and it was considered that even an effective therapy might not be able to reverse the injury in the very sick rats. Only 10 of these rats were selected to receive tolvaptan (5 rats) or vehicle (5 rats) treatment.

The results as shown in FIG. 2 suggest that tolvaptan is very effective in preventing doxorubicin caused mortality if tolvaptan is co-administered with doxorubicin. The ability to reduce mortality is largely lost if the treatment is only initiated after the completion of 6 doxorubicin injections. Thus, a novel finding of this study is that vasopressin antagonists need to be given either before or co-administered with chemotherapy agents to have a protective effect.

Example 2

Figure 3:
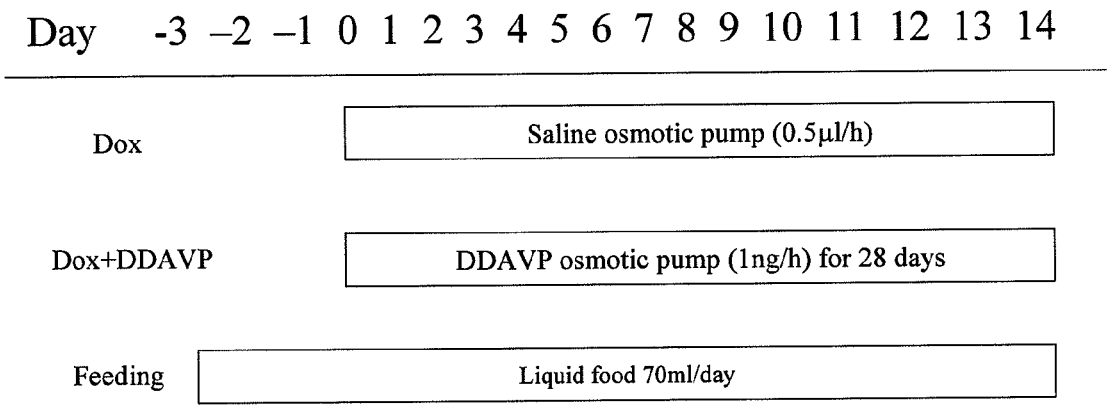
FIG. 3 shows the protocol for the DDAVP (a vasopressin agonist [deamino-Cys1, D-Arg8]-vasopressin) study of Example 2.

The present inventors investigated whether activation of $V_2$ receptors can accelerate doxorubicin-induced mortality. A continuous subcutaneous infusion of 1 ng/h of DDAVP (deamino-Cyst, D-Arg-vasopressin) per animal was accomplished using an osmotic minipump (infusion rate: 0.5 µL/h, ALZET model 2002, DURECT Corporation, Cupertino, Calif.) for 14 days. The protocol for this study is shown in FIG. 3. On day 0 an osmotic minipump was implanted subcutaneously. The sham control rats had the same surgical procedure but with only saline in the minipump. The rats were then divided into two groups: one with six intraperitoneal injections of doxorubicin (2.5 mg/kg) during a 13 day period, and one with injections of saline. The rats were fed with liquid food throughout the experiment. With the continuous infusion of DDAVP, liquid food feeding increases systemic volume overload and edema, conditions often observed in CHF patients.

Figure 4:
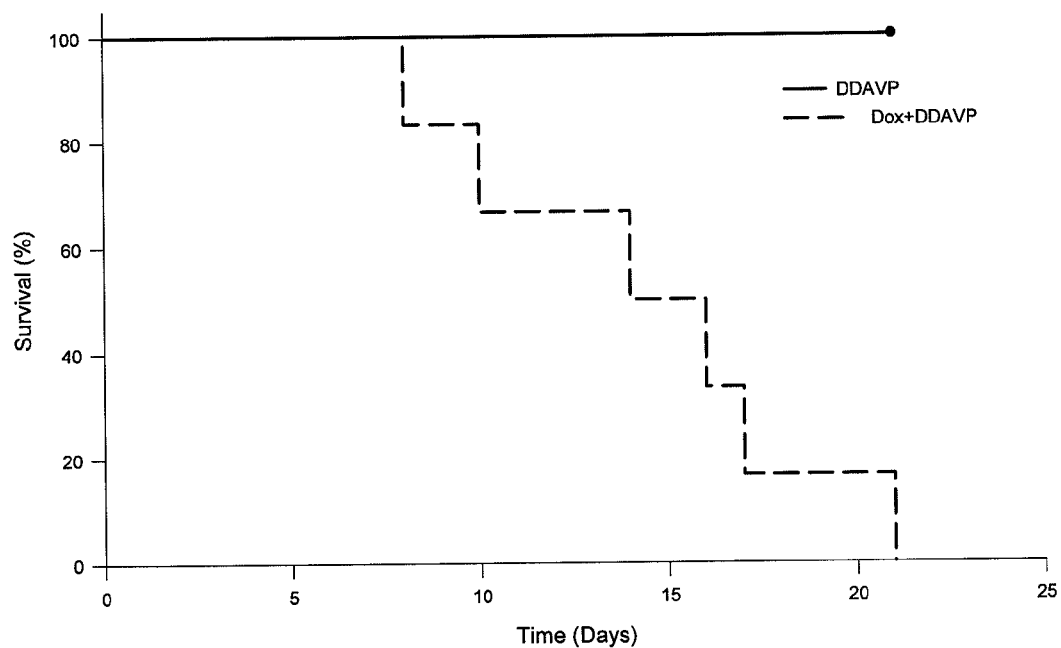
FIG. 4 shows a Kaplan-Meier survival analysis with the Log-Rank test of doxorubicin treated rats.

Supporting the detrimental role of vasopressin $V_2$ receptors in doxorubicin-induced toxicity, DDAVP statistically and significantly increased doxorubicin's toxicity and significantly accelerated the death rate from doxorubicin compared with that of rats treated with doxorubicin alone rats ($p<0.001$, Log-Rank test) as shown in FIG. 4. Thus, in patients treated with doxorubicin, elevated vasopressin levels may further aggravate the toxicity.

Example 3

Figure 5:
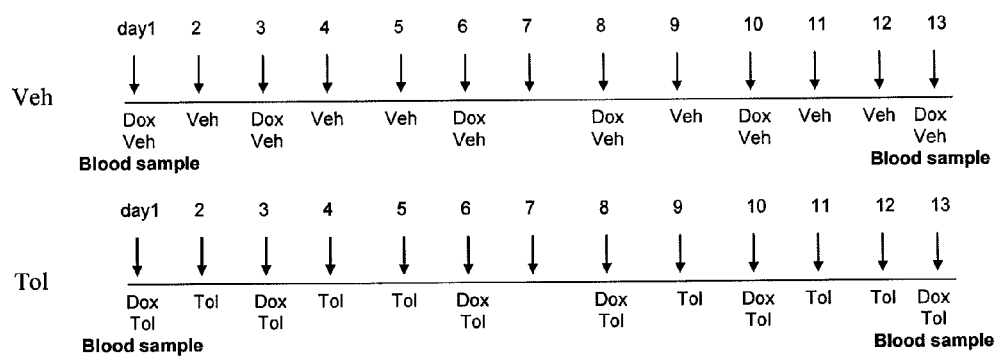
FIG. 5 shows the drug treatment protocol and blood sampling protocol for determining doxorubicin concentration in Example 3.

To determine whether tolvaptan affects the plasma concentration of doxorubicin, plasma samples were obtained after the first (day 1) and sixth (day 13) injection of doxorubicin with vehicle or tolvaptan, and the plasma concentration of doxorubicin was measured. FIG. 5 shows the drug treatment protocol and blood sampling protocol for this study.

Figure 6:
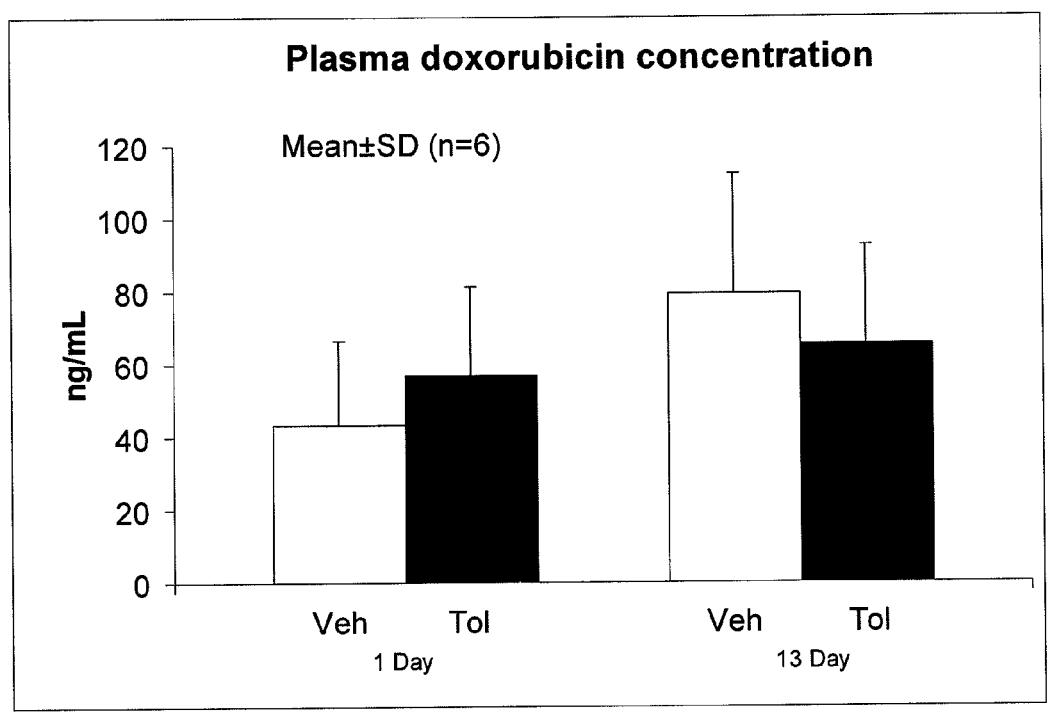
FIG. 6 is a graph showing the results of the effect of tolvaptan on the plasma concentration of doxorubicin.

As shown in FIG. 6, tolvaptan did not affect the plasma concentration of doxorubicin.

Figure 7:
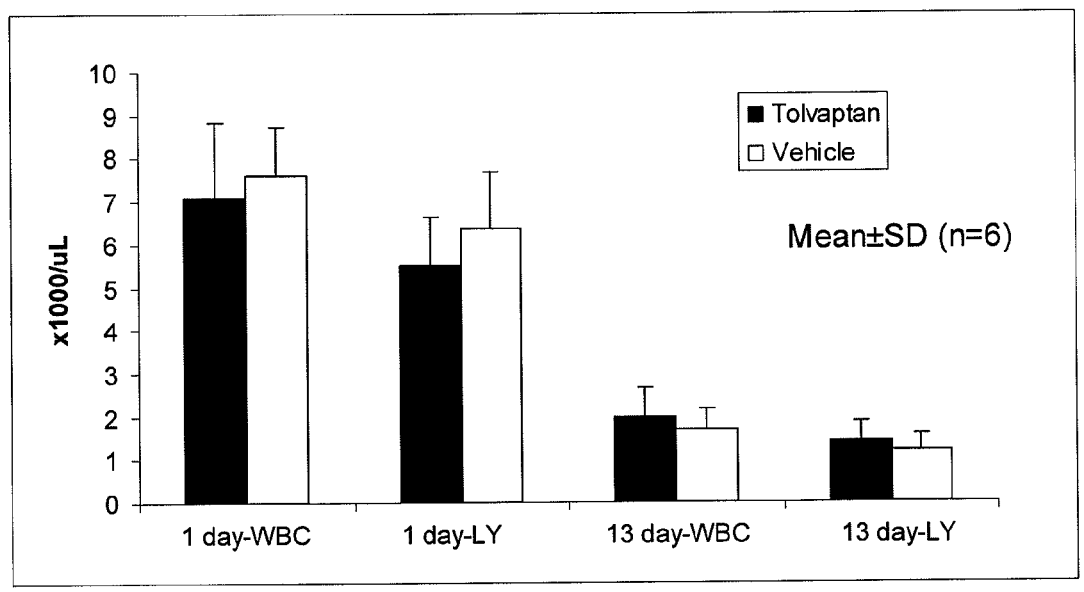
FIG. 7 is a graph showing the effect of tolvaptan on the myelosuppression effect of doxorubicin.

Anthracyclines including doxorubicin are known to cause myelosuppression due to their ability to intercalate into DNA, and to inhibit new protein synthesis and cell proliferation in the bone marrow (similar mechanisms are involved in the inhibition of cancer cell proliferation). Myelosuppression was used as an index of the ability of doxorubicin to inhibit cell proliferation and anti-cancer effect. Tolvaptan did not affect the myelosuppresive effect of doxorubicin as shown in FIG. 7, which shows that a thirteen-day treatment with doxorubicin significantly reduced total white blood cell (WBC) and lymphocyte (LY) counts. Blood samples were taken after 1 or 13 days of treatment with doxorubicin. The decreases in blood cell counts were similar between vehicle- and tolvaptan-treated rats. One day treatment with doxorubicin did not affect blood cell counts.

These results suggest that tolvaptan is unlikely to affect the anti-cancer effect of doxorubicin.

Example 4

In a clinical setting, doxorubicin is administered intravenously to cancer patients. Furthermore, the major side effect associated with doxorubicin treatment is cardiac dysfunction and development of CHF. Therefore, the effect of tolvaptan on CHF was evaluated in a rat model with intravenous injection of doxorubicin. Cardiac function was determined using high resolution ultrasonograpy.

Methods:

Rats were divided into 3 groups as described in Table 2, and observed for 10 weeks.

TABLE 2

The treatment groups for the model of intravenous injection of doxorubicin.

| | Group Name | Drug Dose or Concentration | Number of Rats Included in Data Analysis |
|---|---|---|---|
| 1 | Control | no treatment | 8 |
| 2 | Dox + Veh-Echo (Echo study) | Doxorubicin was injected 3 times (3 mg/kg each, intravenously every other day). Oral vehicle was given daily | 13 |
| 3 | Dox + Tol-Echo (Echo study) | Doxorubicin was injected 3 times (3 mg/kg each, intravenously every other day). Oral tolvaptan (10 mg/kg) was given daily | 12 |

Dox: doxorubicin,
Tol: tolvaptan,
Veh: vehicle.

Control rats were not treated. For groups 2 and 3 with doxorubicin treatment, rats were given three injections intravenously of doxorubicin (3 mg/kg each) every other day (total dose of 9 mg/kg). A lower dose of doxorubicin was chosen in this experiment (compared with the dose in Example 1) to allow the development of CHF during the 10-week period. Rats were given either vehicle or tolvaptan (10 mg/kg) daily starting on the first day of doxorubicin injection. On the days with co-administration of doxorubicin and tolvaptan, tolvaptan was given by oral gavage 45 min prior to the intravenous injection of doxorubicin.

Cardiac function was evaluated using echocardiography (Vevo 770, Visualsonics Inc, Toronto, Canada). Echo images were taken once a week for 10 consecutive weeks. Rats were anesthetized with Isoflurane and parasternal long and short axis echo images were recorded. Offline analysis of cardiac function (ejection fraction and fraction shortening) and anatomic data of the heart (LV end diastolic diameter and volume) were performed. At the end of the 10-week period, cardiac contractility (LVdp/dtmax/ip) was measured invasively.

Figure 8:
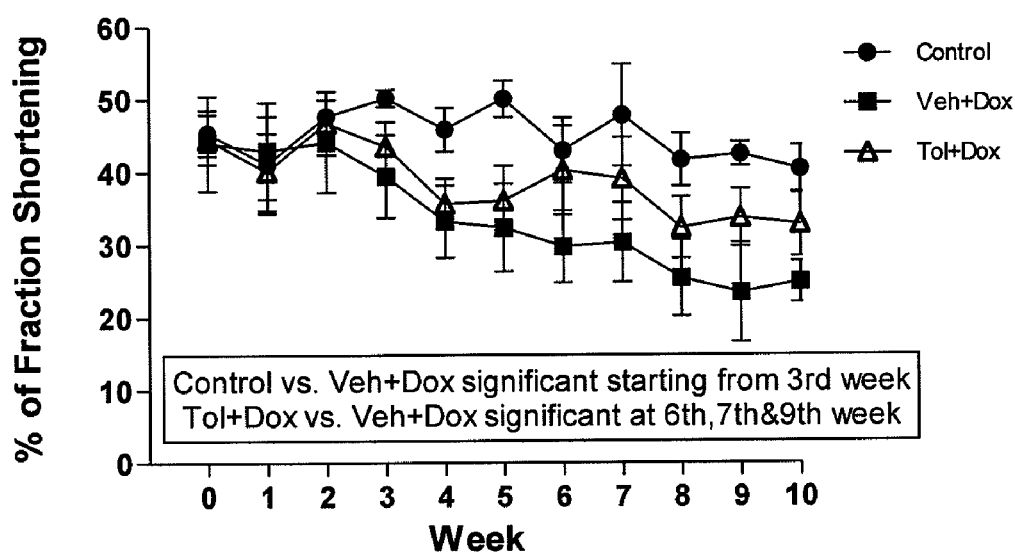
FIG. 8 is a graph showing the percentage of fractional shortening of the left ventricle after tolvaptan treatment in an intravenous injection model.
Figure 9:
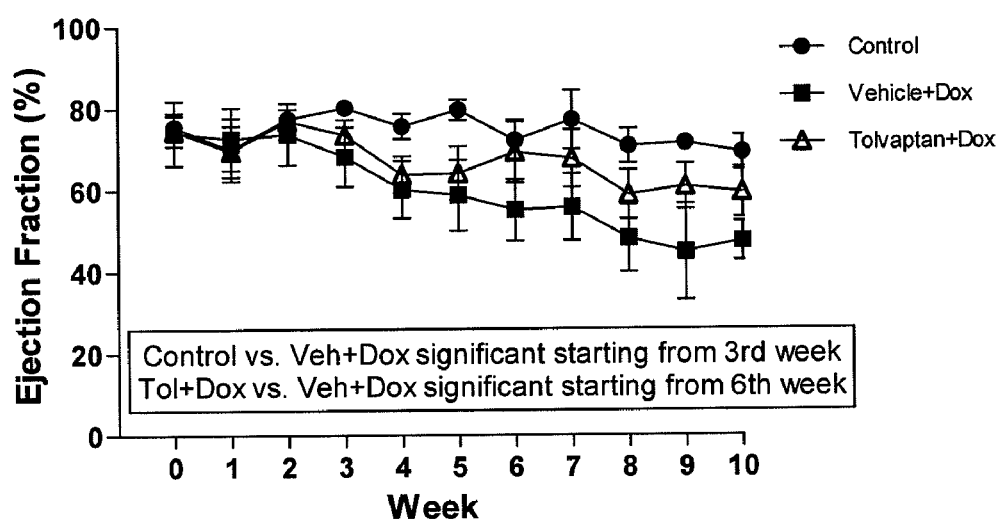
FIG. 9 is a graph showing the ejection fraction of the left ventricle after tolvaptan treatment in an intravenous injection model.

Results:

Data are presented as Mean±SD (standard derivation). Doxorubicin-treatment progressively decreased both fractional shortening and ejection fraction of the left ventricle, indicating heart failure, as shown in FIGS. 8 and 9. Tolvaptan significantly improved cardiac function and slowed the development of heart failure.

Figure 10:
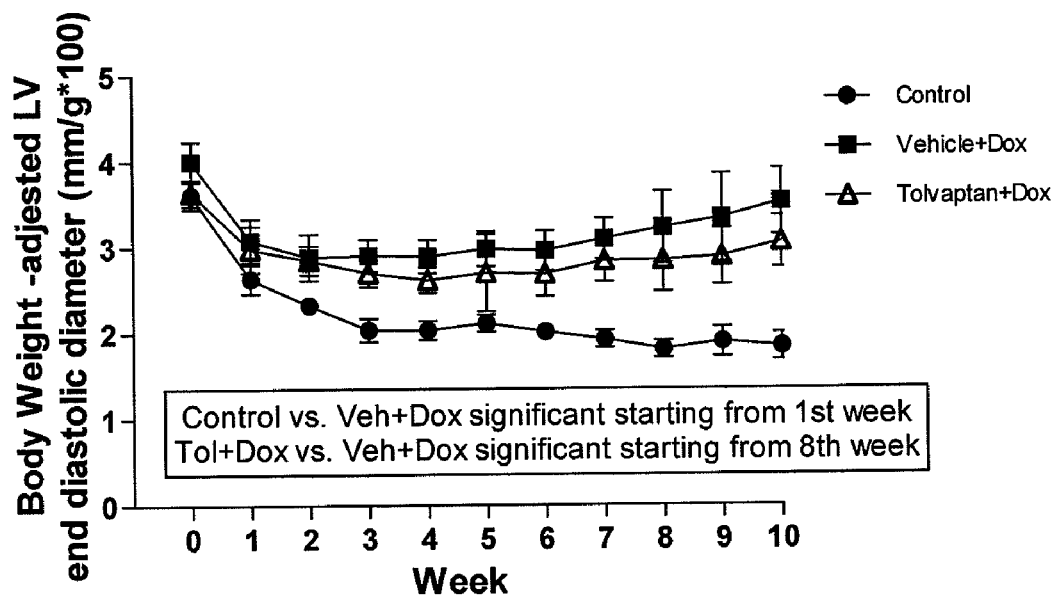
FIG. 10 is a graph showing left ventricle end-diastolic volume/weight adjusted in doxorubicin treated rats.
Figure 11:
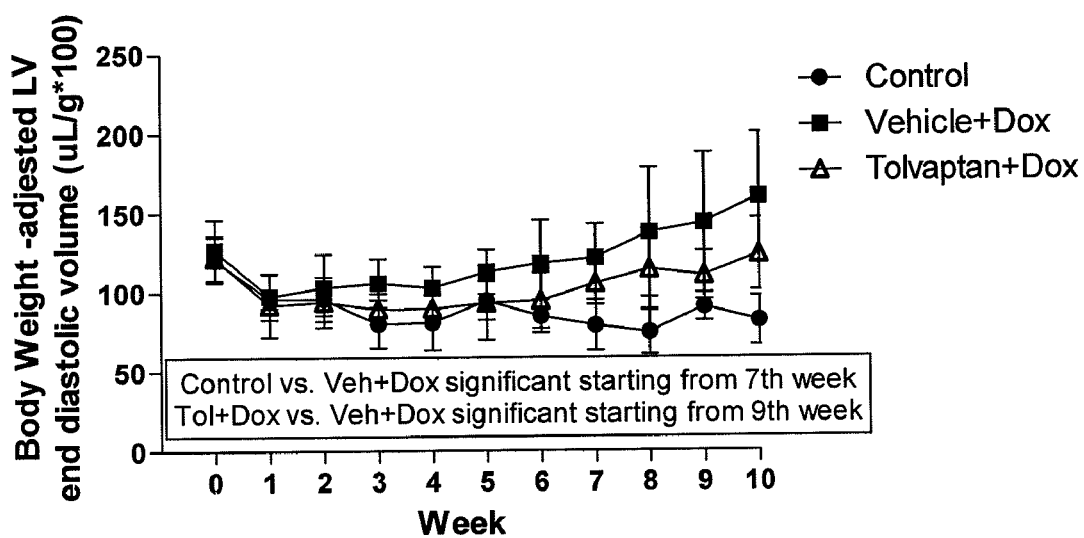
FIG. 11 is a graph showing left ventricle end-diastolic diameter/weight adjusted in doxorubicin treated rats.

In addition to cardiac dysfunction, hallmarks of CHF also include remodeling of the left ventricle: chamber becomes larger and dilated. Indeed, Echo imaging data showed that left ventricle diastolic volume and diameter were progressively increased by doxorubicin-treatment as shown in FIGS. 10 and 11. Tolvaptan slowed the remodeling process.

Figure 12:
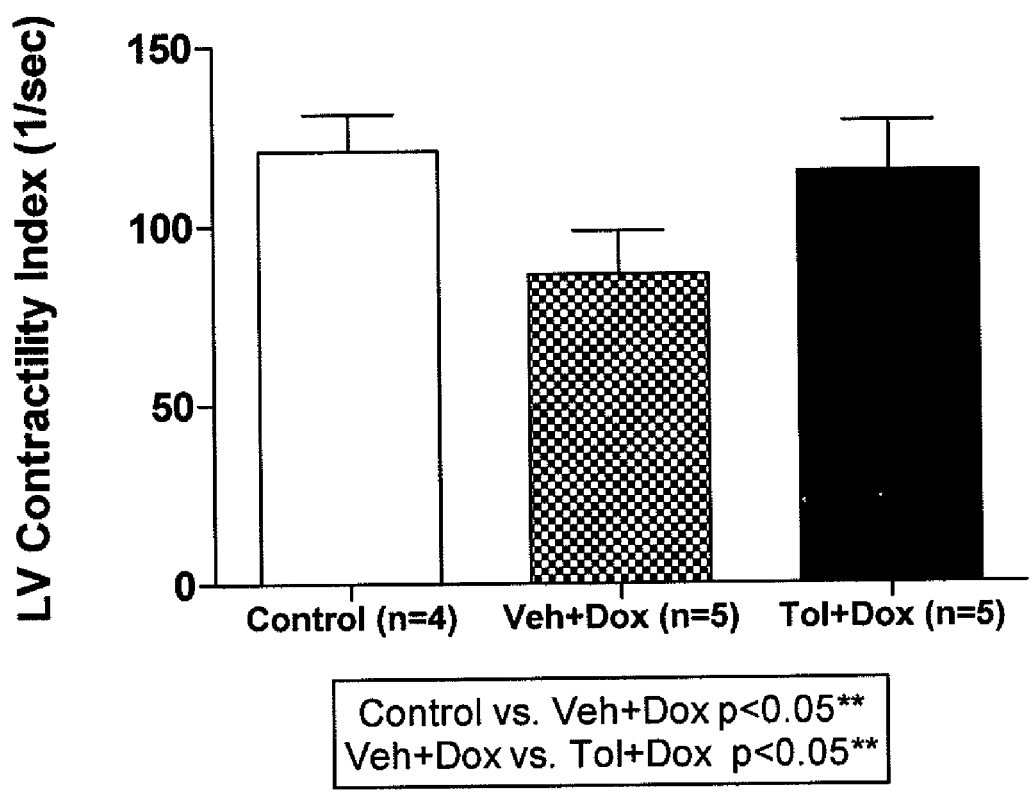
FIG. 12 shows improvement of the contractility index of tolvaptan treated rats.

Invasive hemodynamic measurements were performed at the end of the 10 week period. The contractility index, as defined by the normalization of LVdp/dtmax to instantaneous LV pressure at the LVdp/dtmax, was higher in the tolvaptan-treated rats compared with that in the vehicle-treated rats as shown in FIG. 12.

Example 5

The present inventors investigated whether tolvaptan can improve survival under a sustained activation of $V_2$ receptor (by continuous infusion of a $V_2$ agonist DDAVP) condition in rats treated with intravenous injection of doxorubicin. This condition may be relevant to certain cancer patients who have elevated vasopressin release and are undergoing chemotherapy, such as with doxorubicin.

Figure 13:
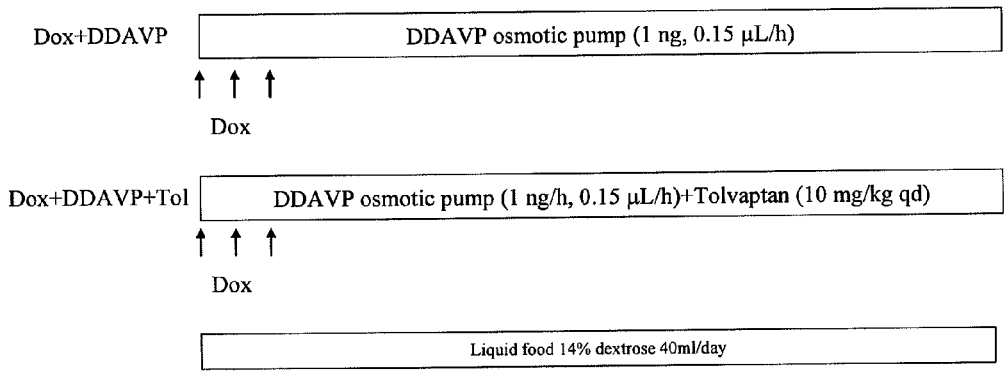
FIG. 13 shows the study protocol of Example 5 to investigate whether a $V_2$ agonist worsens doxorubicin toxicity.

Two groups of rats were studied and the protocol is described in FIG. 13. Rats were intravenously injected with doxorubicin (3 mg/kg) 3 times once every other day for a total of 9 mg/kg (same as described in Example 4). One group (Dox+DDAVP) was given vehicle and the other group (Dox+DDAVP+Tol) was administered tolvaptan (10 mg/kg) once daily. An osmotic minipump (infusion rate: 0.15 µl/h, ALZET model 2006, ALZA Corporation) was implanted in each rat for continuous subcutaneous infusion of 1 ng/h of DDAVP (a vasopressin $V_2$ agonist [deamino-Cys1, D-Arg8]-vasopressin).

Figure 14:
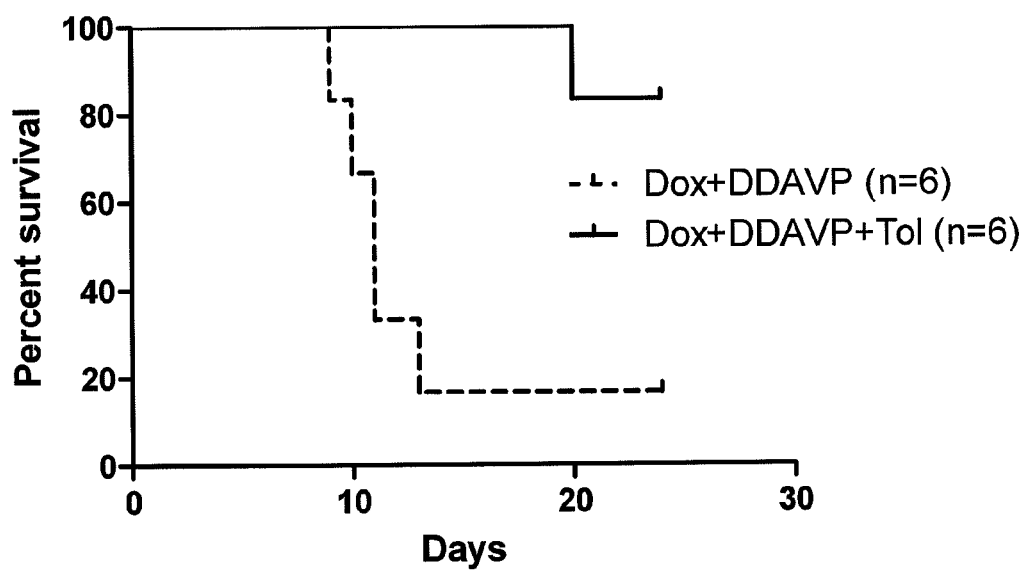
FIG. 14 shows a Kaplan-Meier Survival Analysis e of rats treated with tolvaptan with elevated vasopressin release.

The Kaplan-Meier Survival Analysis is shown in FIG. 14. While infusion of DDAVP made the doxorubicin very toxic and rats died in 2 weeks, tolvaptan significantly improved survival. These data suggest that the toxicity of doxorubicin is enhanced under elevated vasopressin condition. Tolvaptan may be especially useful to reduce doxorubicin toxicity in cancer patients with elevated vasopressin.

All patents, patent applications, scientific and medical publications mentioned herein are hereby incorporated by reference in their entirety. It should be understood, of course that the foregoing relates only to preferred embodiments of the present invention and that numerous modifications or alterations may be made by those of ordinary skill in the art without departing from the spirit and scope of the invention as set forth in the appended claims.

REFERENCE LIST (1) Christiansen S, Autschbach R. Doxorubicin in experimental and clinical heart failure. *Eur J Cardiothorac Surg* 2006 October; 30(4):611-6.
(2) Iarussi D, Indolfi P, Casale F, Martino V, Di Tullio M T, Calabro R. Anthracycline-induced cardiotoxicity in children with cancer: strategies for prevention and management. *Paediatr Drugs* 2005; 7(2):67-76.
(3) Swain S M, Whaley F S, Ewer M S. Congestive heart failure in patients treated with doxorubicin: a retrospective analysis of three trials. *Cancer* 2003 Jun. 1; 97(11):2869-79.
(4) Singal P K, Iliskovic N. Doxorubicin-induced cardiomyopathy. *N Engl J Med* 1998 Sep. 24; 339(13):900-5.
(5) Krischer J P, Epstein S, Cuthbertson D D, Goorin A M, Epstein M L, Lipshultz S E. Clinical cardiotoxicity following anthracycline treatment for childhood cancer: the Pediatric Oncology Group experience. *J Clin Oncol* 1997 April; 15(4):1544-52.
(6) Lipshultz S E, Rifai N, Dalton V M et al. The effect of dexrazoxane on myocardial injury in doxorubicin-treated children with acute lymphoblastic leukemia. *N Engl J Med* 2004 Jul. 8; 351(2):145-53.
(7) Cvetkovic R S, Scott L J. Dexrazoxane: a review of its use for cardioprotection during anthracycline chemotherapy. *Drugs* 2005; 65(7):1005-24.
(8) Swain S M, Whaley F S, Gerber M C et al. Cardioprotection with dexrazoxane for doxorubicin-containing therapy in advanced breast cancer. *J Clin Oncol* 1997 April; 15(4):1318-32.
(9) Brenner B, Rector F. *The Kidney*. 7th ed. Philadelphia, Pa.: Saunders; 2004.
(10) Tang W H, Bhavnani S, Francis G S. Vasopressin receptor antagonists in the management of acute heart failure. *Expert Opin Investig Drugs* 2005 May; 14(5):593-600.
(11) Campling B G, Sarda I R, Baer K A et al. Secretion of atrial natriuretic peptide and vasopressin by small cell lung cancer. *Cancer* 1995 May 15; 75(10):2442-51.
(12) Mizobuchi M, Kunishige M, Kubo K, Komatsu M, Bando H, Saito S. Syndrome of inappropriate secretion of ADH (SIADH) due to small cell lung cancer with extremely high plasma vasopressin level. *Intern Med* 1994 August; 33(8):501-4.
(13) North W G. Gene regulation of vasopressin and vasopressin receptors in cancer. *Exp Physiol* 2000 March; 85 Spec No: 27S-40S.
(14) North W G, Pai S, Friedmann A, Yu X, Fay M, Memoli V. Vasopressin gene related products are markers of human breast cancer. *Breast Cancer Res Treat* 1995 June; 34(3):229-35.
(15) Talmi Y P, Hoffman H T, McCabe B F. Syndrome of inappropriate secretion of arginine vasopressin in patients with cancer of the head and neck. *Ann Otol Rhinol Laryngol* 1992 November; 101(11):946-9.
(16) Umemura S, Segawa Y, Ueoka H et al. Serum level of arginine-vasopressin influences the prognosis of extensive-disease small-cell lung cancer. *J Cancer Res Clin Oncol* 2007 August; 133(8):519-24.
(17) Ma J, Fan S, Chen J, Gu Y, Lin S. Messenger RNA expressions of vasopressin system and aquaporin-2 in adriamycin-induced nephrotic rats and effects of astragalus membranaceus. *Chin Med J (Engl)* 1999 December; 112(12):1068-72.
(18) Johnston C I, Arnolda L, Abrahams J, McGrath B. Role of vasopressin in experimental congestive cardiac failure. *J Cardiovasc Pharmacol* 1986; 8 Suppl 7:S96-100.
(19) Price J F, Towbin J A, Denfield S W et al. Arginine Vasopressin Levels Are Elevated and Correlate With Functional Status in Infants and Children With Congestive Heart Failure. *Circulation* 2004 May 17.
(20) Burrell L M, Phillips P A, Risvanis J, Chan R K, Aldred K L, Johnston C I. Long-term effects of nonpeptide vasopressin V2 antagonist OPC-31260 in heart failure in the rat. *Am J Physiol* 1998 July; 275(1 Pt 2):H176-H182.
(21) Francis G S, Tang W H. Vasopressin receptor antagonists: will the "vaptans" fulfill their promise? *JAMA* 2004 Apr. 28; 291(16):2017-8.
(22) Xu D L, Martin P Y, Ohara M et al. Upregulation of aquaporin-2 water channel expression in chronic heart failure rat. *J Clin Invest* 1997 Apr. 1; 99(7):1500-5.
(23) Burrell L M, Risvanis J, Johnston C I, Naitoh M, Balding L C. Vasopressin receptor antagonism—a therapeutic option in heart failure and hypertension. *Exp Physiol* 2000 March; 85 Spec No: 259S-65S.
(24) Gheorghiade M, Niazi I, Ouyang J et al. Vasopressin V2-receptor blockade with tolvaptan in patients with chronic heart failure: results from a double-blind, randomized trial. *Circulation* 2003 Jun. 3; 107(21):2690-6.
(25) Takeuchi M, Lee J D, Shimizu H, Ueda T. Effects of long-term oral treatment with selective vasopressin V2 receptor antagonist (OPC-31260) on adriamycin-induced heart failure in rats. *Int J Cardiol* 2006 Apr. 4; 108(2):231-6.

What is claimed is:

1. A method for reducing cardiotoxicity and/or improving survival from anthracycline chemotherapy comprising administering to a patient in need thereof a therapeutically effective amount of a composition comprising a vasopressin antagonist compound or a pharmaceutically acceptable salt thereof as the active ingredient, administered simultaneously with or prior to anthracycline administration.

2. The method of claim 1, for reducing cardiotoxicity.

3. The method of claim 1, for improving survival.

4. The method of claim 1, wherein the vasopressin antagonist is a compound represented by formula (I):

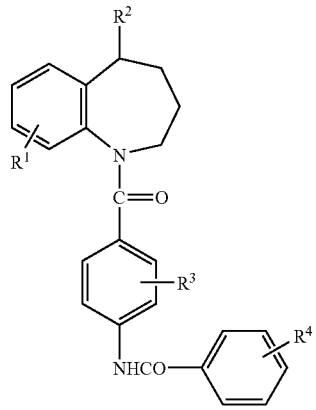

Formula (I)

wherein $R^1$ is a hydrogen atom or a halogen atom, $R^2$ is a hydroxy group, or a group of the formula: —$NR^5R^6$ wherein $R^5$ and $R^6$ are the same or different and are each a hydrogen atom or a lower alkyl group, $R^3$ is a hydrogen atom, a halogen atom, a lower alkyl group, or a lower alkoxy group, $R^4$ is a halogen atom, a lower alkyl group or a lower alkoxy group, or a pharmaceutically acceptable salt thereof.

5. The method of claim 1, wherein the vasopressin antagonist is selected from the group consisting of tolvaptan, mozavaptan, conivaptan, lixivaptan, satavaptan, RWJ-351647, RWJ-339489, SSR-149415, YM-222546, YM-471, YM-35471, YM-218, FR-218944, JNJ-17079166, JNJ-17308616, VMAX-367, VMAX-382, VMAX-372, ORG-52186, SRX-251 and a pharmaceutically acceptable salt thereof.

6. The method of claim 1, wherein the vasopressin antagonist is a $V_2$ selective vasopressin antagonist or a $V_1/V_2$ vasopressin antagonist.

7. The method of claim 1, wherein the anthracycline is selected from the group consisting of daunorubicin, doxorubicin, epirubicin, and idarubicin.

8. The method of claim 1, wherein the vasopressin antagonist is tolvaptan.

9. The method of claim 1, wherein the vasopressin antagonist is mozavaptan hydrochloride.

10. The method of claim 1, wherein the vasopressin antagonist is conivaptan hydrochloride.

11. The method of claim 1, wherein the vasopressin antagonist is lixivaptan.

12. The method of claim 1, wherein the vasopressin antagonist is satavaptan.

13. The method of claim 1, wherein the vasopressin antagonist is tolvaptan and the anthracycline is daunorubicin.

14. The method of claim 1, wherein the vasopressin antagonist is tolvaptan and the anthracycline is doxorubicin.

15. The method of claim 1, wherein the vasopressin antagonist is tolvaptan and the anthracycline is epirubicin.

16. The method of claim 1, wherein the vasopressin antagonist is tolvaptan and the anthracycline is idarubicin.

* * * * *